United States Patent [19]
Svenson et al.

[11] Patent Number: 5,715,819
[45] Date of Patent: Feb. 10, 1998

[54] MICROWAVE TOMOGRAPHIC SPECTROSCOPY SYSTEM AND METHOD

[75] Inventors: Robert H. Svenson, Charlotte, N.C.; Serguei Y. Semenov; Vladimir Y. Baranov, both of Moscow, Russian Federation

[73] Assignee: The Carolinas Heart Institute, Charlotte, N.C.

[21] Appl. No.: 250,762

[22] Filed: May 26, 1994

[51] Int. Cl.⁶ .................................................... A61B 5/05
[52] U.S. Cl. ........................................ 128/653.1; 324/637
[58] Field of Search .......................... 128/653.1; 600/10, 600/2; 606/27, 32–34; 607/89, 101; 324/637, 638, 639; 364/481, 482

[56] References Cited

U.S. PATENT DOCUMENTS

| | | | |
|---|---|---|---|
| 4,135,131 | 1/1979 | Larsen et al. | 128/653.1 |
| 4,247,815 | 1/1981 | Larsen et al. | 128/653.1 |
| 4,662,222 | 5/1987 | Johnson | 73/602 |
| 4,798,209 | 1/1989 | Klingenbeck et al. | 128/653.1 |
| 4,805,627 | 2/1989 | Klingenbeck et al. | 128/653.1 |
| 4,926,868 | 5/1990 | Larsen | 128/653.1 |
| 5,222,501 | 6/1993 | Ideker et al. | 128/660.03 |
| 5,305,748 | 4/1994 | Wilk | 128/653.1 |
| 5,363,050 | 11/1994 | Guo et al. | 128/653.1 |
| 5,405,346 | 4/1995 | Grundy et al. | 607/101 |

*Primary Examiner*—Brian L. Casler
*Attorney, Agent, or Firm*—Patterson & Keough, P.A.

[57] ABSTRACT

The invention is a system for non-invasive microwave tomographic spectroscopy of tissue using a plurality of microwave emitter-receivers spatially oriented to the tissue, an interface medium placed between the emitter-receivers, and a control subsystem operably coupled to the plurality of microwave emitter-receivers for selectively controlling power to the plurality of emitter-receivers and for receiving microwave signals from the plurality of emitter-receivers so that multiple frequency microwave radiation is emitted from a selected plurality of emitter-receivers and received by a selected plurality of emitter-receivers after interacting with and passing through the tissue, and a computational subsystem operably connected to the control subsystem for computing a tomographic spectroscopic image of the tissue from the microwave signals received from the selected plurality of emitter-receivers.

36 Claims, 13 Drawing Sheets

MICROWAVE TOMOGRAPHIC SPECTROSCOPY SYSTEM AND METHOD

FIELD OF THE INVENTION

The invention is related to microwave tomographic imaging and in particular to imaging biological tissues to obtain internal structural imaging as well as functional imaging.

BACKGROUND OF THE INVENTION

Microwave tomographic imaging uses microwave radiation to image an object by detecting the effects the object had on the microwave beam after it has interacted with the object. With microwave radiation, it is the dielectric permittivity and conductivity properties of the tissues of the object being imaged that determines the nature of the interaction. The dielectric permittivity and conductivity properties of an object are expressed together as a complex permittivity.

Microwaves, as a component of the electromagnetic radiation spectrum, are in the frequency range between approximately 0.1 Giga Hertz GHz to 300 GHz. This corresponds to the wavelength range between 300 mm and 1 mm. The microwave range useful for microwave imaging of biological tissues is in the range from about 0.5 to about 3 GHz, but other ranges of the microwave spectrum can be used as well. The quantum energy of the photons in this range of the electromagnetic spectrum comprises non-ionizing radiation.

In general, microwave imaging differs from X-rays, positron emission, ultrasound, or nuclear magnetic resonance imaging because the microwave radiation interacts with the object to be imaged as a function of the complex permittivity of the object. Complex permittivity is made up of the dielectric permittivity and the dielectric loss. The dielectric permittivity is the real part and is given by the equation:

$$\epsilon' = \epsilon/\epsilon_0. \qquad \text{Equation 1}$$

The relative dielectric loss is given by the imaginary part as $$\epsilon'' = \frac{\sigma}{2\pi f \epsilon_0}. \qquad \text{Equation 2}$$

Where $\epsilon_0$ is the dielectric permittivity of vacuum, $\sigma$ is the conductivity of the material and f is the working frequency. For example, water has a fairly broadband dielectric permittivity, being approximately 80 at about 1 GHz and falling to about 4.5 at frequencies higher than 100 GHz. Water dielectric loss increases from values at about 1 GHz to around 25 GHz. An additional factor affecting the permittivity of water is its temperature.

There are two basic categories of microwave imaging. The first category is static imaging based on forming images by determining the absolute permittivity values of the microwave radiation after its interaction with the object. The second category is dynamic imaging which is based on variations in permittivity within the object occurring at the time of incidence of the microwave radiation. This second form of imaging is extremely useful in applications for imaging biological tissues to monitor ongoing physiologic change. It must be understood, however, that both static imaging and dynamic imaging still require an active imaging process whereby a microwave scanner employs moving or scanning incident radiation and detects the changes in the microwave radiation based on interaction with the object being imaged.

Most non-biological objects that are amenable to imaging by microwaves are very simple structures in terms of dielectric and conductivity variability. On the other hand, biological tissues demonstrate a wide range of relative dielectric constants. These ranges are thought to be due in large part to the interaction of the microwave radiation with charges on the surface of cellular membranes, the actual structure of the cellular membrane with its hydrophobic layer between the hydrophilic layers, and the water and electrolyte content both within and without the cellular structures. Consequently, biological tissue interaction is extremely complex and will even change with time due to the subtle change in temperature secondary to the absorption of the microwave energy used to obtain the microwave image. This absorption is converted to heat, especially by water. This is quite important because the average biological tissue contains approximately 70% water.

Tomographic microwave imaging has used a series of microwave emitters and receivers arrayed spatially around an object to be imaged. In a 1990 publication in IEEE Transactions on Biomedical Engineering, vol. 37 no. 3; pp. 303–12, March, 1990, titled "Medical Imaging with a Microwave Tomographic Scanner", Jofre et al., disclose a cylindrical array of microwave emitters and receivers. The array totalled 64 waveguide antennas in four groups of 16 antennas. Each waveguide antenna is capable of function as an emitter or receiver. The object to be imaged is placed within the array circle and immersed in water to minimize attenuation of the microwave incident beam as it interacts with the surface of the object. Each antenna within a group emits in sequence and the 16 antennas in the group opposite the emitting group act as receivers. This procedure is sequentially repeated for each antenna until one revolution is completed. The output microwave signal was 2.45 GHz, providing a collimated field approximately 2 cm in height and having a power density of less than 0.1 milliwatt per square centimeter at the object.

The Jofre et. al structure uses a coherent phase quadrature detector to measure the magnitude and phase of the signal from the receiving antennas. The data is digitized and a computer performs a reconstruction of the image based on changes in the microwave radiation. This reconstruction is carried out by an algorithm formulated to yield an approximation of the microwave diffraction in two dimensions. The algorithm makes use of the Born approximation which assumes that scattering acts as a small perturbation on the illumination and therefore the field within the body is approximated by the incident field. This approximation problem remains as a substantial limitation to microwave tomography.

In a publication in Journal of Neuroscience Methods, 36; pp. 239–51, 1991, entitled "Active Microwave Computed Brain Tomography: The Response to a Challenge", Amirall et al., disclose an application of the cylindrical array in Jofre's paper to imaging the brain. The image was again reconstructed using a diffraction algorithm for cylindrical geometries using Fast Fourier Transform techniques and the Born first order approximation.

The data as reconstructed through the algorithm generates a contrast in permittivity values of a cut of the body as a function of the spatial coordinates of the portion of the imaged body creating that contrast in permittivity. Resolving power theoretically is limited to diffraction values of one half the wavelength of the microwave radiation. For a frequency of 2.45 GHz this would mean a theoretical minimum resolution of about 6 cm in air and 7 mm in water. As a consequence of the reconstruction algorithms and limitations in the electronics used in the devices, these theoretical values are not achieved.

The validity of the first order approximations and the algorithms used in the above device limit imaging to static images of small bodies such as limbs. In the case of larger bodies, such as a human head, the reconstructed image would only show correctly the outer contour of the body but not the internal structure.

Using dynamic imaging, image reconstruction is based on the difference in diffracted fields recorded from several data sets taken from a body with a changing dielectric contrast. Amirall et al., were able to achieve internal imaging within the larger bodies, however, resolution was approximately only half the theoretical predictions.

SUMMARY OF THE INVENTION

The invention is a system for non-invasive microwave tomographic spectroscopy of tissue using a plurality of microwave emitter-receivers spatially oriented to the tissue, an interface medium placed between the emitter-receivers, control means operably coupled between a power source and the plurality of microwave emitter-receivers for selectively controlling power to the plurality of emitter-receivers and for receiving microwave signals from the plurality of emitter-receivers so that multiple frequency microwave radiation is emitted from a selected plurality of emitter-receivers and received by a selected plurality of emitter-receivers after interacting with and passing through the tissue, and computational means operably connected to the control means for computing a tomographic spectroscopic image of the tissue from the microwave signals received from the selected plurality of emitter-receivers.

The invention includes a method for non-invasive microwave tomographic spectroscopy of tissue using steps of providing a microwave radiation power source, providing a plurality of microwave radiation emitter-receivers, controlling the plurality of microwave radiation emitter-receivers so that a plurality of emitter-receivers are able to emit multiple microwave frequency radiation from the power source to a plurality of emitter-receivers that are receiving the microwave radiation, placing an interface medium between the emitting and receiving microwave emitter-receivers, placing tissue to be irradiated within the interface medium, emitting the microwave radiation from the microwave emitter-receivers, receiving the microwave radiation in the microwave emitter-receivers after interacting with the tissue, and measuring a change in the microwave radiation after interacting with the tissue.

This invention embodies a method of identifying discrete signals correlating to specific antenna arrays in a microwave tomographic spectroscopy tissue imaging system using steps of providing a microwave tomographic spectroscopy system having a microwave power source, a plurality of microwave emitters-receivers, an interface medium between the microwave emitters-receivers, control means for providing microwave signals to the emitters-receivers and for receiving microwave signals from the emitters-receivers after the microwave signals have interacted with the tissue, orienting a tissue to be imaged in the interface medium, encoding the signals originating simultaneously from different emitters and interacting with the tissue, and decoding the signals received by different receivers so that the signals are distinguishable according to the originating emitter.

This invention also embodies a method of non-invasive microwave tomographic spectroscopy of tissue using the steps of designating a target tissue area for microwave irradiation, determining expected tissue dielectric values for the designated target tissue area, providing a multiple frequency microwave radiation emitting and receiving system having microwave emission means, microwave receiving means and microwave analysis means, irradiating the target tissue area with microwave radiation from the microwave emission means, receiving the microwave radiation from the irradiated target tissue area with the receiving means, analyzing the received microwave radiation with the analysis means to obtain an observed tissue dielectric values, and comparing the observed tissue dielectric values with the expected tissue dielectric values to determine a physiologic state of the tissue within the designated target tissue area.

DETAILED DESCRIPTION OF THE INVENTION

Figure 1:
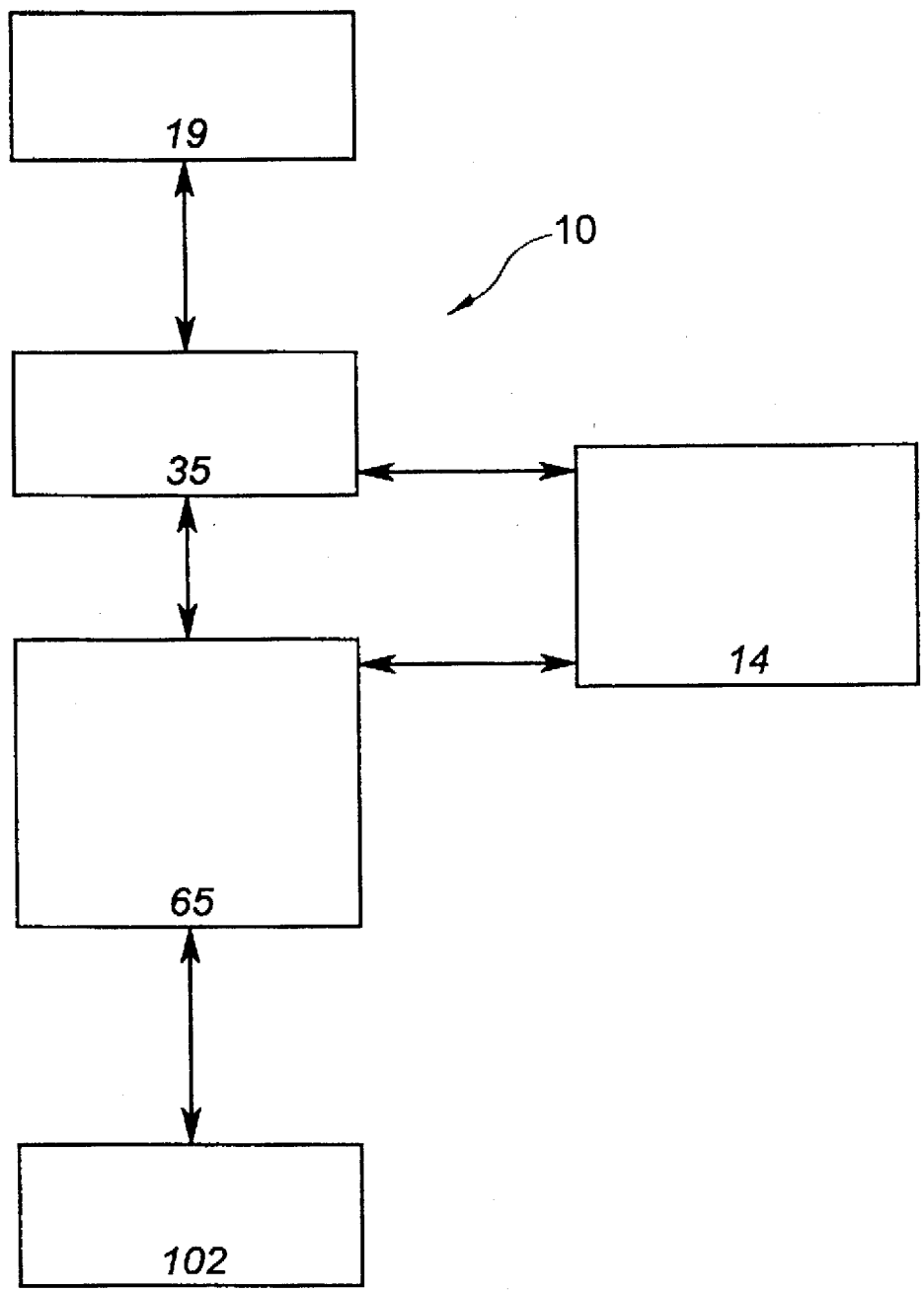
FIG. 1 is a schematic diagram of the microwave tomographic spectroscopy system of the invention.
Figure 2:
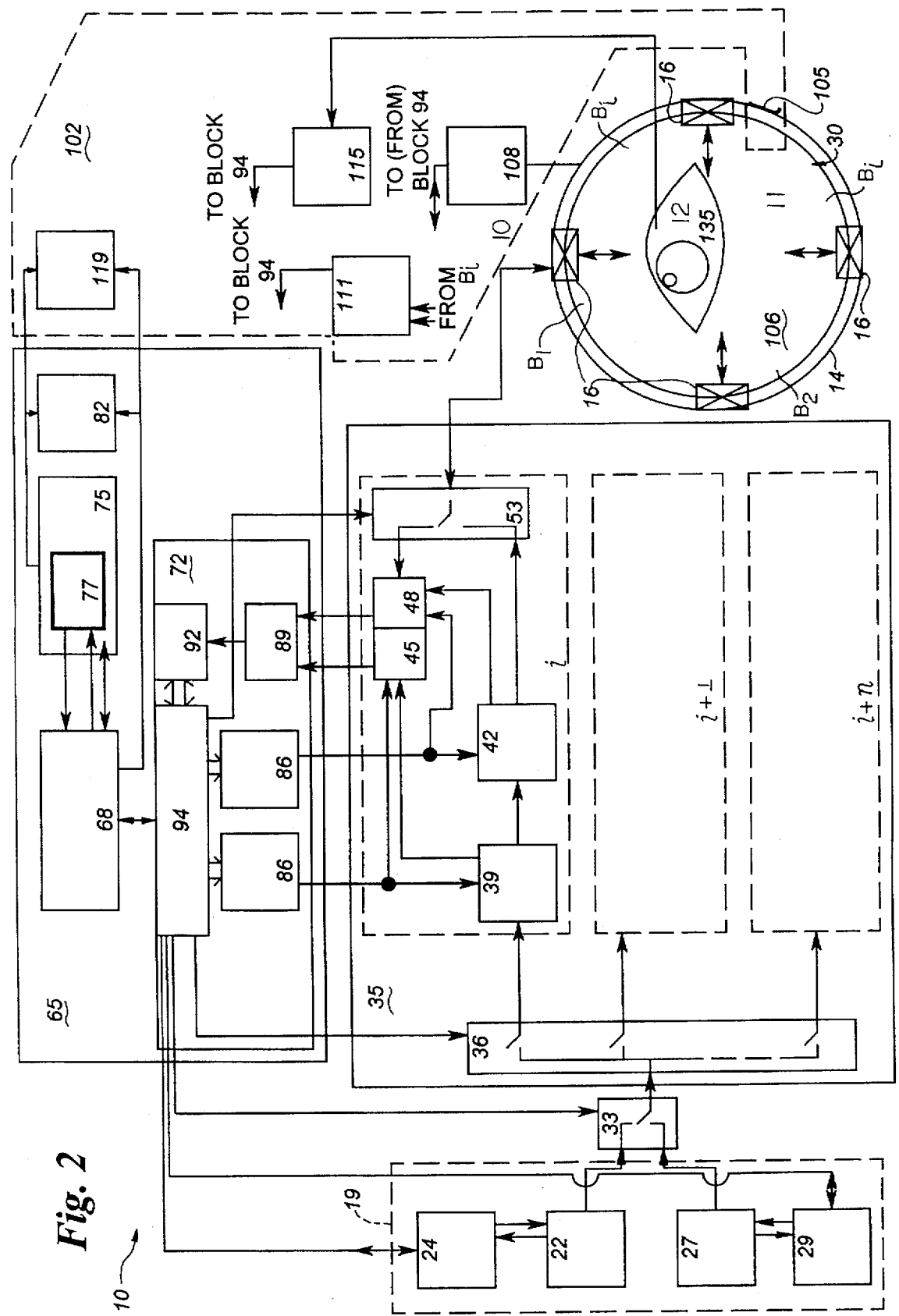
FIG. 2 is a schematic diagram of the microwave tomographic spectroscopy system of the invention.

FIGS. 1 and 2 are each schematic diagrams of the tomographic spectroscopy system 10 of this invention. Utility of this invention encompasses many fields, however the preferred field described below is that of medical uses. More particularly, the embodiments of the invention claimed below relate to non-invasive diagnosis and therapy for heart arrhythmias. The microwave system enables rapid and highly accurate non-invasive detection and localization of cardiac arrhythmogenic foci, as well as non-invasive cardiac mapping capabilities. System 10 accomplishes these procedures using a multiple frequency regimen, signal encoding techniques, improved mathematical algorithms, and previously unrecognized correlation functions. These and other features of the invention will become apparent from the more detailed description below.

Identification of the origin of cardiac arrhythmias has previously depended on one of three principal techniques: catheter mapping, electrical excitation mapping during cardiac surgery, or body surface mapping of electric potentials or magnetic fields. Each of these techniques has substantial risks and limitations. For example, catheter mapping and excitation mapping during surgery are inherently invasive, access limited, and time sensitive. Body surface mapping can be performed in a non-invasive, low risk manner but with such poor definition that the data is generally considered unsuitable for directing therapy. The mapping may be performed using either sequential temporal changes in the electrical potential distribution on the surface of the body or sequential changes in magnetic fields on the body surface.

The invention does not require insertion of a catheter into a body, nor does it require inserting probes into cardiac tissue. However, reliable and precise (2–5 mm) three dimensional reconstruction of the heart and its electrical excitation sequence is now possible using this invention. Use of the techniques listed below for ablation of arrhythmogenic sites is non-invasive and advantageously utilizes the different frequencies and directions of energy available so that the ablation threshold will occur only at the designated location. The invention does anticipate invasive procedures, for example, ablation systems delivered by catheters or surgical procedures to accomplish physician directed therapy.

As briefly mentioned above, the invention utilizes novel correlation functions. These functions relate to tissue physical properties and changes of those properties during cell excitation. In particular, the dielectrical behavior of biological tissue can be defined by two characteristic parameters: dielectric permeability and conductivity. The parameter functions include frequency, temperature, and tissue type. The tissue type parameter provides opportunities for detection of anatomical structure by measuring transmitted, i.e. reflected and scattered, electromagnetic energy through tissue. For homogenous objects the dielectric characteristics can be readily detected by measuring amplitude and phase of transmitted electromagnetic radiation. However, the problem is more complicated when trying to measure the dielectric values of radiation transmitted through non-homogenous biological tissue simply by using measured amplitude and phase of the transmitted wave. This problem is known as the "inverse" or "reverse" problem and has attracted some attention to its solution. This invention incorporates the strong dependance of tissue characteristics on temperature, and solves the "reverse" problem in novel ways by using multiple frequency and multiple position emitter-receiver configurations.

Referring to FIGS. 1 and 2, system 10 comprises microwave emitter-receiver sub-assembly 14 suitable for mounting a plurality of microwave emitters-receivers 16. A preferred configuration of emitters-receivers is in a circular array, and each emitter-receiver 16 may be enabled for radial movement relative to the circular array. Sub-assembly 14 may also comprise a plurality of vertically stacked emitters-receivers. A power source 19 provides narrow pulse-width electromagnetic energy signals to each emitter of not more than about 10 mW/cm$^2$ incident power density on an object. Preferably, the frequency band width of these narrow pulse-width signals is centered between about 0.1 GHz to about 6 GHz, and more preferably within the frequency range of about 0.2 GHz to about 2.5 GHz. Power source 19 may comprise either a plurality of power sources or a single power source, such as a generator. In the embodiment of FIG. 2, power source 19 comprises a sweeping diagnostic generator 22, a diagnostic generator control block 24, an ablation generator 27, and an ablation generator control block 29. Sweeping diagnostic generator 22 provides multiple frequency low power energy for use in diagnostic applications, while ablation generator 27 provides high power energy for microwave ablation of designated tissue regions. Selection of either of the above generators is accomplished by switch 33 which connects generator output with the emitters 16.

A channelization mechanism 35 is provided for activation and control of channels i, i+1, i+n, for energy emission and reception. This subsystem comprises a channel number switch 36, an amplitude attenuator-detector manipulation (ADM) 39, a phase rotator-detector 42, an amplitude detector 45, a phase detector 48, and an antenna mode switch 53. In diagnostic operation, channel number switch 36 connects the output of the diagnostic generator 22 with the input of the emitter (or a multiple of emitters) at any particular time. In the ablation or therapeutic mode, the switch connects all channels with the output of the ablation generator 27. Amplitude attenuator-detector 39 and phase rotator-detector 42 are in the emitter path of all channels. Amplitude attenuator-detector 39 attenuates the amplitude of emitted power, and with phase rotator-detector 42 detects and encodes the output signal. Amplitude detector 45 and phase detector 48 are in the received path of all channels and, in the diagnostic mode, detect and decode the amplitude and phase of the received signal. It is recognized that other coding means, such as polarity, may require additional encoding/de-coding components. Antenna mode switch 53 functions in all channels to connect the output of the emitter path with the antenna or input path, at the receiver path, with the same antenna.

Computation and control module means 65 includes a central processing unit (CPU) 68, an interface subsystem 72, a display 75 and a display software 77, as well as a memory 82. The interface subsystem 72 consists of a digital-to-analog converter(s) (DAC) 86, a multiplexer 89, an analog-to-digital converter (ADC) 92, and a control block 94 which creates time synchronization of controlled processes and receives data to be analyzed.

An auxiliaries subsystem 102 comprises a thermostatic shield 105 for controlling the temperature of an interface medium 106, for example, a fluid such as a solution of titanium and barium having a preliminary dielectrically adjustable dielectric permittivity between about 50 and 90 at 2.45 GHz and a dielectric loss between about 5 and 25, between the emitters-receivers 16, a thermostatic control block 108 for controlling thermostatic shield 105, and a basic channel control block 111 for control of the received signal from the Bi control channels when the system 10 is in a calibration mode. Additional auxiliary components may be added depending on desired performance features of the system, for example, an electrocardiogram analyzer and/or a printer 119 may be useful to the system 10.

Figure 3:
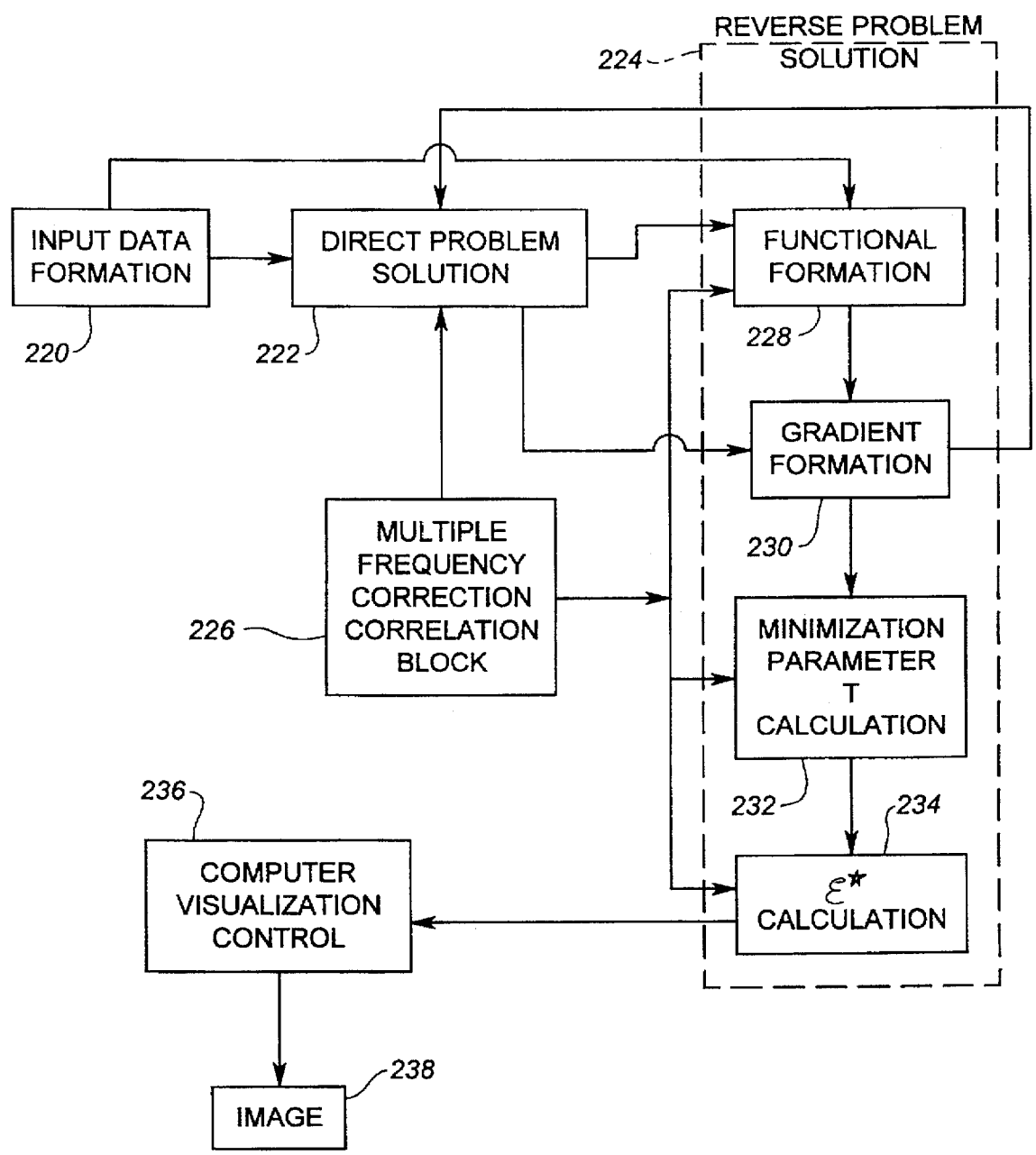
FIG. 3 is a flow diagram of the algorithm for the reverse problem solution.

In a sequential multiple frequency tomographic spectroscopy system 10, target tissue 135 is irradiated in sequence with low energy microwave radiation from the first to the n$^{th}$ emitter (receiver) 16, while simultaneously taking measurement of the received signals in (emitter) receivers 16 which in that particular step of the sequence are not functioning as an emitter. Several emitter-receivers 16 are used to receive signals emitted by a single emitter-receiver 16 in any given instance of time. The system 10 rapidly changes channel number and antenna mode in sequence according to the above configuration. After one cycle of n-channel emissions and receptions, sweeping diagnostic generator 22 provides another cycle of n-channel switched measurements. The total quantity of cycle measurements is normally not more than N×M, where N is the quantity of antennas, and M is the quantity of used diagnostic frequencies. It is also recognized that simultaneous measurements may be obtained using a multiple encoded frequency configuration. Following the measurements, system 10 solves the "reverse" problem according to the received information and the novel algorithms described more fully below in relation to FIGS. 3 and 4. When measuring physiologic changes it is important to understand the time it takes for a physiologic event to occur, for example a myocardial contraction. These time periods are defined as tissue event time cycles.

Data acquisition in system 10 is performed in time intervals which are a fraction of a tissue event time cycle so that data acquisition may occur many times during each tissue event and are stored in memory 82. Reconstruction time is fast enough that body motion is not a problem. Anatomical object structure and temperature profiles are observable on display 75, may be manipulated using routines of display software 77, and may be printed using printer 119. The arrhythmogenic zones of the heart are defined as those regions with particular $\epsilon'$ and $\epsilon''$ values. Spatial coordinates of these zones are defined with the help of the display software, the CPU, and the memory.

During measurement cycles, system 10 periodically makes temperature control corrections of the interface medium 106 with the aide of the thermostatic control block 108. System 10 also synchronizes with the heart cycle in which the tissue is resident using electrocardiogram analyzer 115.

A key feature of system 10 which facilitates the speed and accuracy of calculation is the use of a coding device for encoding the microwave signals supplied to the emitters. When the receivers receive the corresponding signals after interaction with the tissue, the signals are distinguishable by their originating emitter or emitter group. Preferred encoding techniques are phase, amplitude, or polarity modulation; however it is also within the scope of the invention to employ frequency modulation. Frequency modulation may be useful in certain applications where simultaneous emissions from a plurality of emitters are required.

System 10 is one embodiment for using the novel method steps of this invention which permits non-invasive microwave tomographic spectroscopy of tissue. The method comprises the steps of: providing a microwave radiation power source; providing a plurality of microwave radiation emitter-receivers; and controlling the plurality of microwave radiation emitter-receivers so that a plurality of emitter-receivers are able to emit multiple microwave frequency radiation from the power source to a plurality of emitter-receivers that are receiving the microwave radiation. Further steps include: placing an interface medium between the emitting and receiving microwave emitter-receivers for dielectric matching; placing tissue to be irradiated within the interface medium; emitting the microwave radiation from the microwave emitter-receivers; receiving the microwave radiation in the microwave emitter-receivers after interacting with the tissue; and measuring a change in the microwave radiation after interacting with the tissue.

As disclosed above, novel algorithms are used to solve the "reverse" problem calculations. In this invention, there are no approximations, such as the Born approximation discussed above, used to define dielectric or conductivity parameters of non-homogenous irradiated tissue objects. Rather, the measuring step of the above method incorporates both old and new concepts to refine and render useful the data derived from this form of electromagnetic imaging. In particular, and as shown in the flow diagram of FIG. 3, the measuring steps comprise computations using an input data formation component 220, a direct problem solution component 222, a reverse problem solution component 224, a multiple frequency correlation component 226, a computer visualization control 236, and a tomographic spectroscopic image 238.

The direct problem solution is a known calculation which solves microwave propagation from emitter to receiver through a biological means. Solution of the reverse problem allows precise computation and generation of a tomographic spectroscopically useful image of the tissue based on the measured change of the microwave radiation. The reverse problem solution steps comprise: determination of a functional formation component 228 which sums the input from all emitters-receivers; using a gradient formation component 230 as a derivative of the functional formation component to simplify processing speed; calculating a minimization parameter tau to verify the accuracy of the gradient function and to reconstruct in the most accurate manner; and performing an E* calculation 234. The E* calculation 234 uses the following:

$$\epsilon^* = \epsilon' + i\epsilon'' \qquad \text{Equation 3}$$

Where $\epsilon'$ said $\epsilon''$ are the values of dielectric permittivity and loss measured by the invention and i represents the imaginary number. Using $\epsilon^*$ as a representative value of $\epsilon'$ and $\epsilon''$ is a convenient mathematical tool. It should be understood that the invention may also use either $\epsilon'$ and/or $\epsilon''$ as the measured dielectric parameter for generating an image. The reason for using $\epsilon^*$ is that dielectric contrast between tissue and/or tissue physiologic states may be found in either a difference or change in $\epsilon'$ and/or $\epsilon''$. If $\epsilon'$ and $\epsilon''$ are calculated together as $\epsilon^*$ then any dielectric change in either $\epsilon'$ or $\epsilon''$ will be detected in an $\epsilon^*$ calculation. As will be seen later, some physiological dielectric changes are best evaluated by using only $\epsilon'$ or $\epsilon''$. It is important to recognize that wherever $\epsilon^*$ is used, $\epsilon'$ or $\epsilon''$ can also be used in place of $\epsilon^*$.

Figure 4:
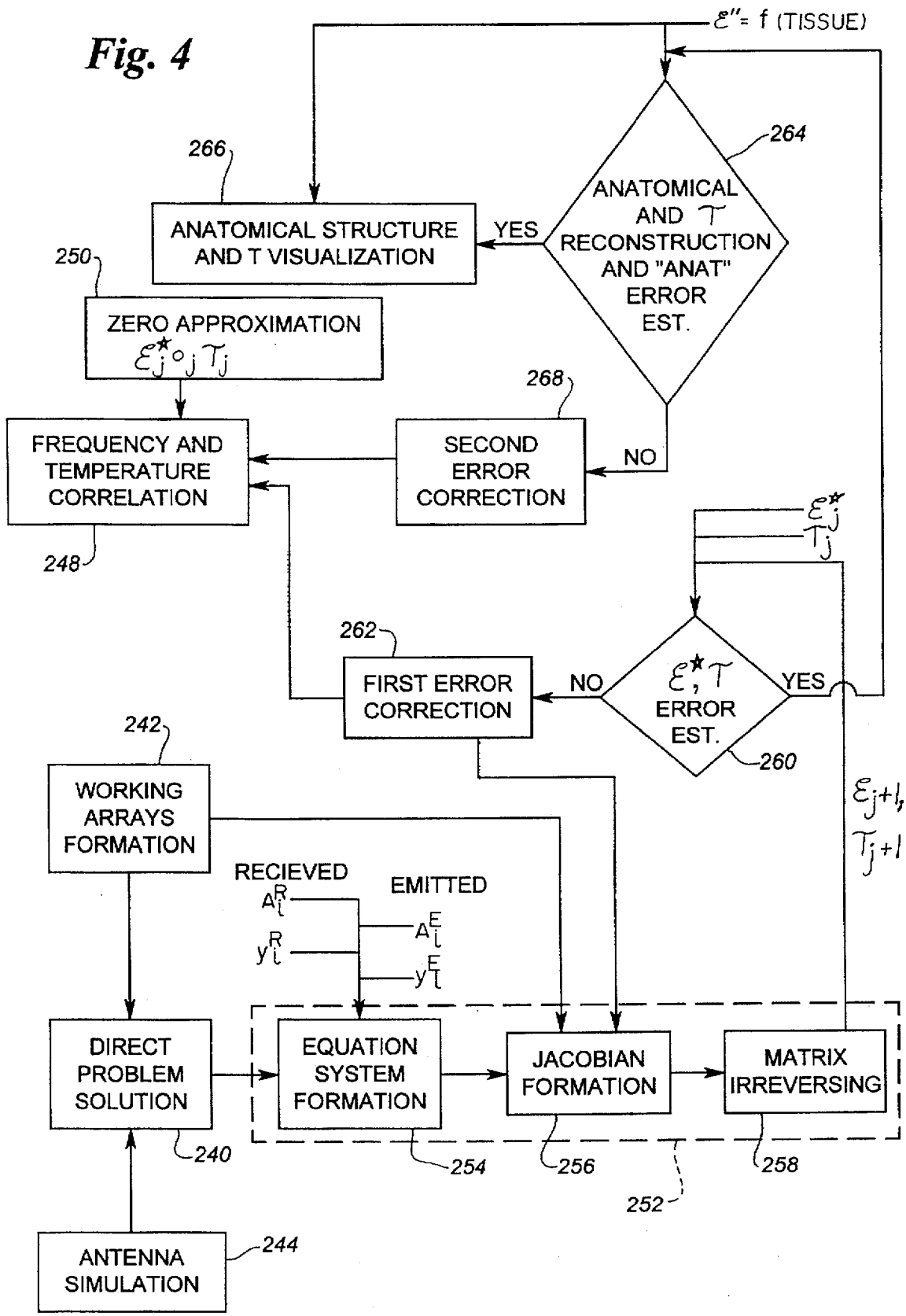
FIG. 4 is a flow diagram of an alternate reconstruction algorithm for the reverse problem solution.

The flow chart depicted in FIG. 4 represents an embodiment of the present invention for use in a catheter delivered microwave tomographic system. Data is fed into a direct problem solution step 240 from a working arrays formation step 242 and an antenna simulation step 244. The working arrays formation step 242 receives data from a frequency and temperature correlation step 248 which derived its initial values from a zero approximation step 250. The antenna simulation step 244 provides values for starting the calculation process acting as a base line from which to construct an image. Direct problem solution step 240 then is able to solve an image problem based on knowing what the amplitude and phase of the emitted microwave energy is and making an assumption as to what the biological tissue dielectric effects will be and calculating an expected amplitude and phase value for the transmitted microwave energy. This solution from the direct problem solution step 240 is then passed to reverse problem solution step 252 comprising an equation system formation step 254, a Jacobian formation step 256, and a matrix irreversing step 258. The reverse problem solution step 252 then calculates an image of the biological tissue based on known emitted microwave amplitude and phase values and known received amplitude and phase values from the emitter receiver arrays. In effect, the reverse problem solution is generating the tomographic image by knowing the amplitude and phase of the emitted microwave energy and the amplitude and phase of the transmitted or received microwave energy in order to calculate the dielectric characteristics of the biological tissue through which the microwave energy has passed. This image data from the matrix irreversing step 258 is then passed through an error correcting iteration process involving an error estimation step 260 and a first error correction step 262. For each value of amplitude and phase emitted and received, where i is equal to 1–n, the matrix irreversing step 258 in conjunction with error estimation 260 and first error correction 262 forms an iterative loop that begins with inputing the first grid point $\epsilon *\Delta T$ into the error estimation step 260. For each value of i, from 1–n, a $\epsilon *_{j+1}$, $T_{j+1}$ is generated in which j is the grid number in the coordinate system for generating the two or three dimensional image construct and where j is equal to values from 1–n. After each $\epsilon *$, T value has undergone an error estimation and first error correction, the value is then passed to an anatomical and T reconstruction and anatomy error estimation step 264. At this point the value as fed into error estimation step 264 is compared with the $\epsilon ''$ value and if the error estimation has occurred the value is passed onto an anatomical structure and T visualization step 266 which serves the purpose of generating the two dimensional or three dimensional image of the biological tissue based on dielectric contrast. If, however, the error estimation step results in a no response, a data point is passed to a second error correction step 268 which then adjusts, in conjunction with the first correction step 262, the values generated by frequency and temperature correlation step 248.

Figure 5:
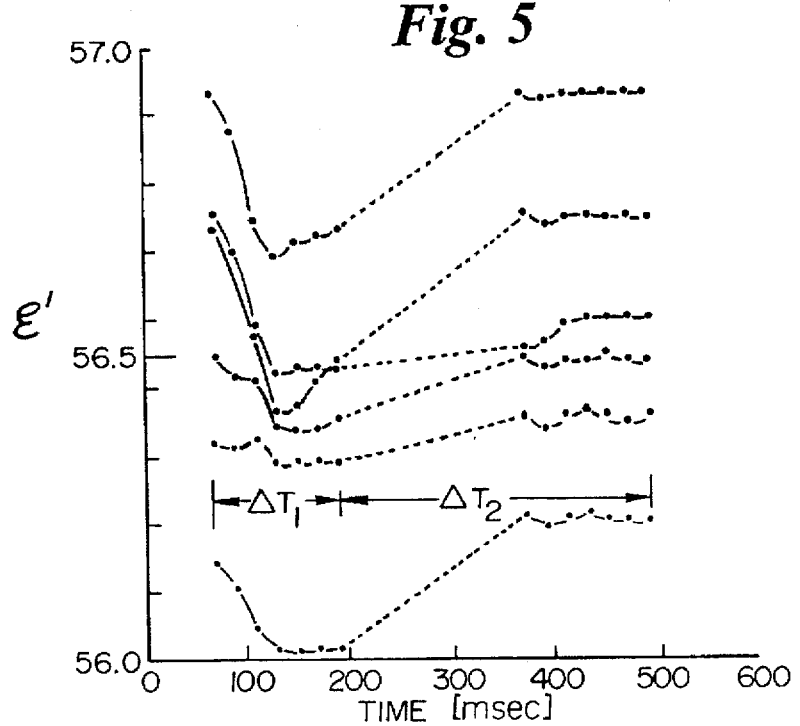
FIG. 5 is a graph of canine cardiac tissue dielectric characteristics as a function of heart cycle.
Figure 6:
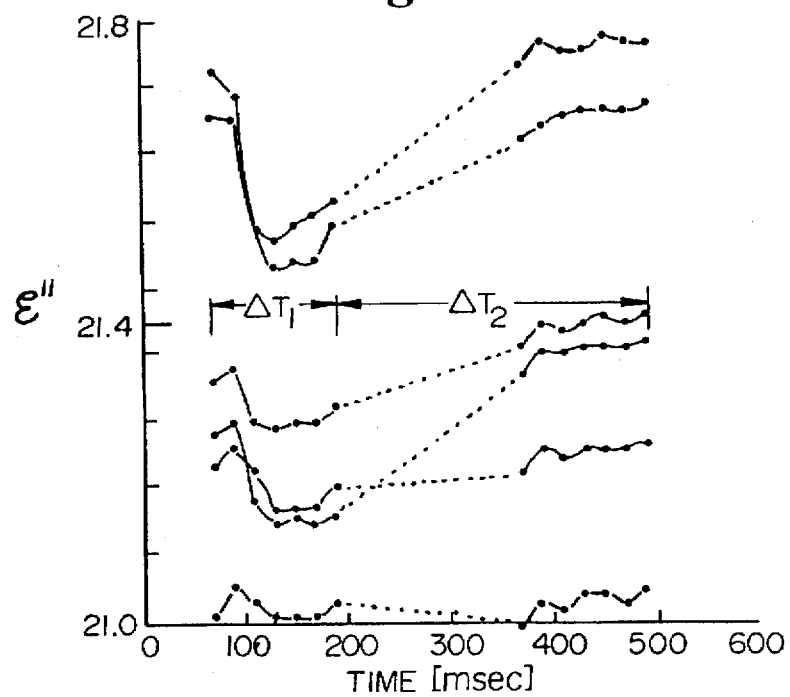
FIG. 6 is a graph of canine cardiac tissue dielectric characteristics as a function of heart cycle.

FIG. 5 is a graph demonstrating the capability of system 10 to detect cardiac excitation by changes in dielectric characteristics of cardiac tissue. In particular, FIG. 5 shows the change in $\epsilon '$ values at the onset and throughout the period $\Delta T_1$ of an electrical excitation process and during the transition period $\Delta T_2$ to recovery. FIG. 6 discloses similar detection capabilities for system 10, but for values of the $\epsilon ''$ dielectric parameter. In both FIGS. 5 and 6, each point represents a mean value for seven measurements.

Figure 7:
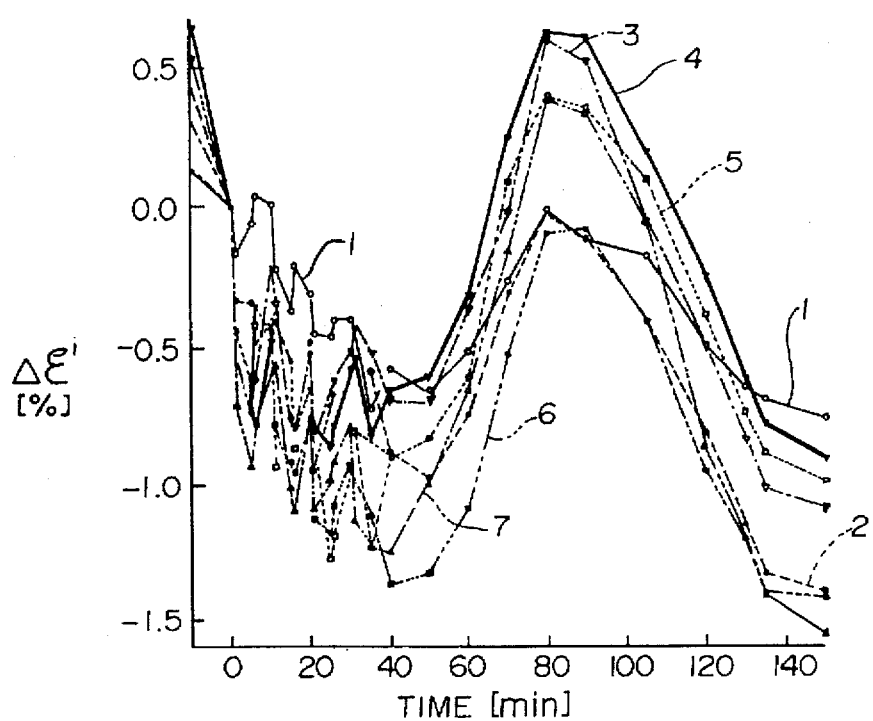
FIG. 7 is a graph of canine cardiac tissue dielectric characteristics as a function of occlusion and re-perfusion.
Figure 8:
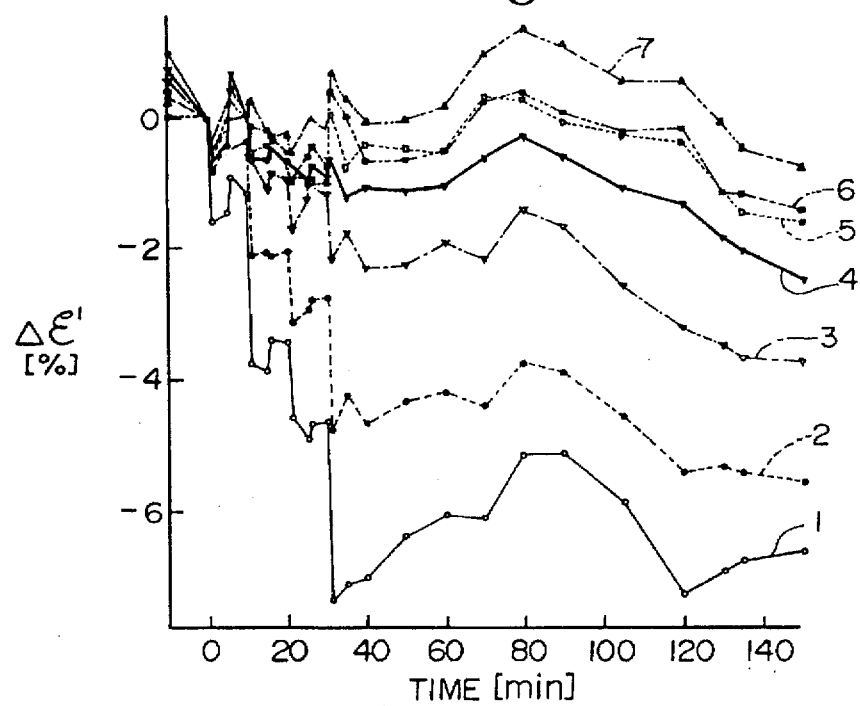
FIG. 8 is a graph of canine cardiac tissue dielectric characteristics as a function of occlusion and re-perfusion.
Figure 9:
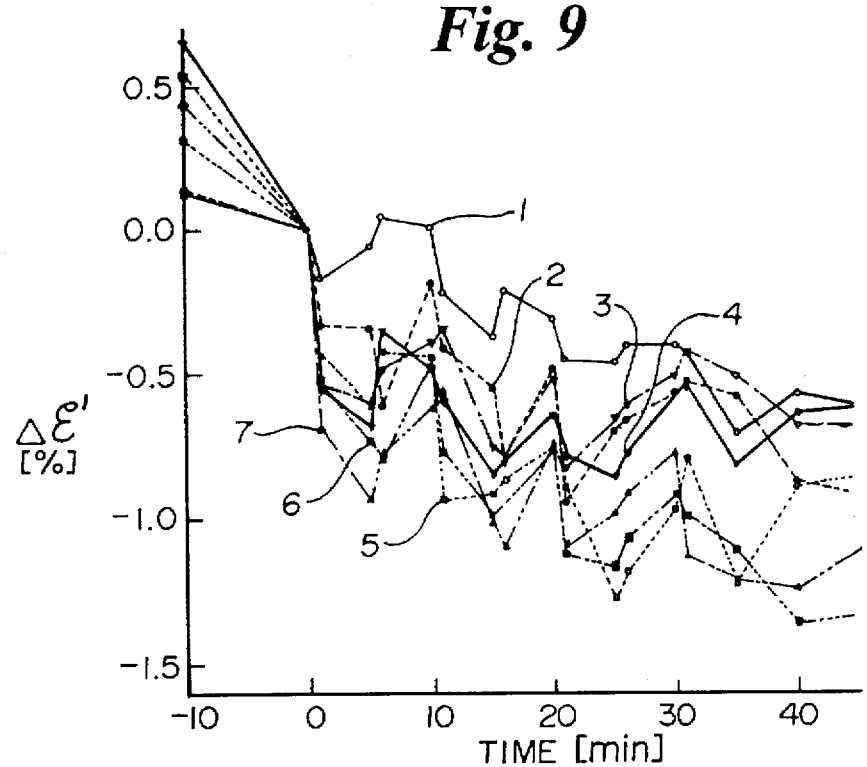
FIG. 9 is a graph of canine cardiac tissue dielectric characteristics as a function of occlusion and re-perfusion.
Figure 10:
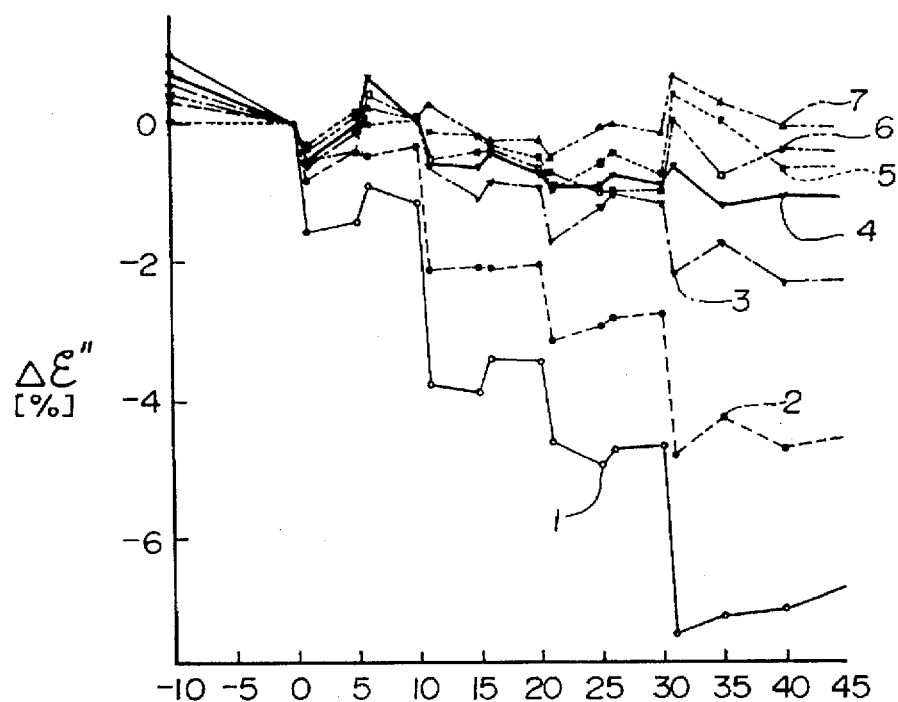
FIG. 10 is a graph of canine cardiac tissue dielectric characteristics as a function of occlusion and re-perfusion.

FIGS. 7–10 are graphs demonstrating the percent change of a selected dielectric characteristic, for multiple frequencies, during a series of coronary arterial occlusions. FIGS. 7 and 8 disclose, over a long duration, a series of short occlusions followed by a long occlusion. These figures demonstrate the correlation of dielectric characteristics for $\epsilon '$ and $\epsilon ''$ depending on the degree of cardiac ischemia. This pattern of dielectric changes conforms with the known tissue phenomenon of a protective effect from pre-conditioning prior to a total occlusion. FIGS. 9 and 10 disclose, over a short duration, a series of short occlusions followed by a long occlusion. These figures support the conclusions stated above in relation to FIGS. 7 and 8.

Figure 11:
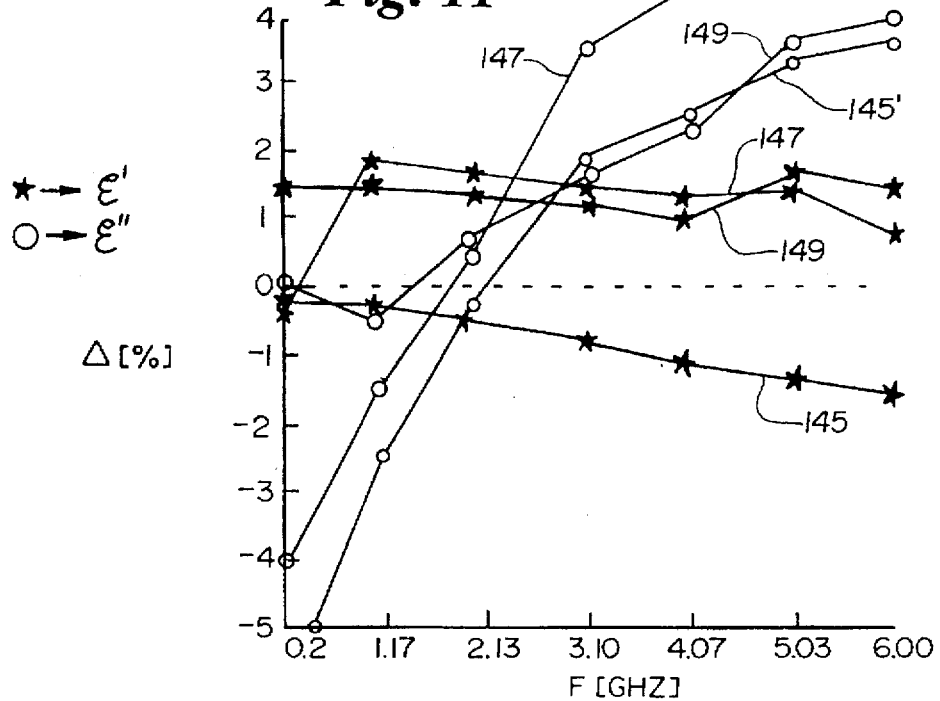
FIG. 11 is a graph of canine cardiac tissue first order and second order dielectric characteristics as a function of time and frequency of microwave emission.
Figure 12:
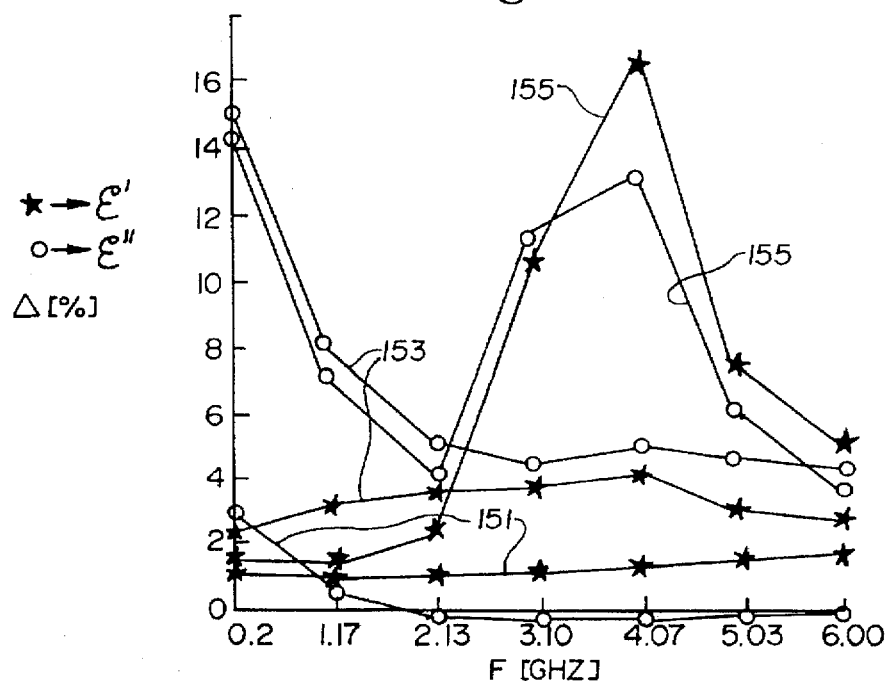
FIG. 12 is a graph of canine cardiac tissue first order and second order dielectric characteristics as a function of time and frequency of microwave emission.

FIG. 10 provides further example of the value of multiple frequency or spectroscopic analysis of tissue. In this figure, the curve of the values of percent change of $\epsilon ''$ at 4.1 GHz is relatively flat and less useful as compared to the corresponding values at either 0.2 GHz or 1.17 GHz. This highlights the need for system 10 to detect tissue excitation phenomena and other physiological events, e.g. ischemia, using multiple frequency techniques which might otherwise remain undetected or not useful in a single frequency analysis. This is further demonstrated in the $\epsilon *(f)$ graphs of FIGS. 11 and 12, in which curves 145, 147, 149, 151, 153, and 155 represent time after occlusion (i.e., acute ischemia) of 0, 15, 30, 45, 120, and 125 minutes respectively for $\epsilon '$ (shown by * curves) and $\epsilon ''$ (shown by o curves). The value of $\Delta$ is $\Delta\epsilon */\epsilon *$ before. Reperfusion occurs at time 125 minutes, and is represented by curves 155. These figures demonstrate that if analysis is limited to a single frequency, then very little useful data is derived during short tissue excitation periods. However, if multiple frequency analysis is conducted essentially simultaneously then the tissue physiological phenomena are clearly exhibited.

Figure 13:
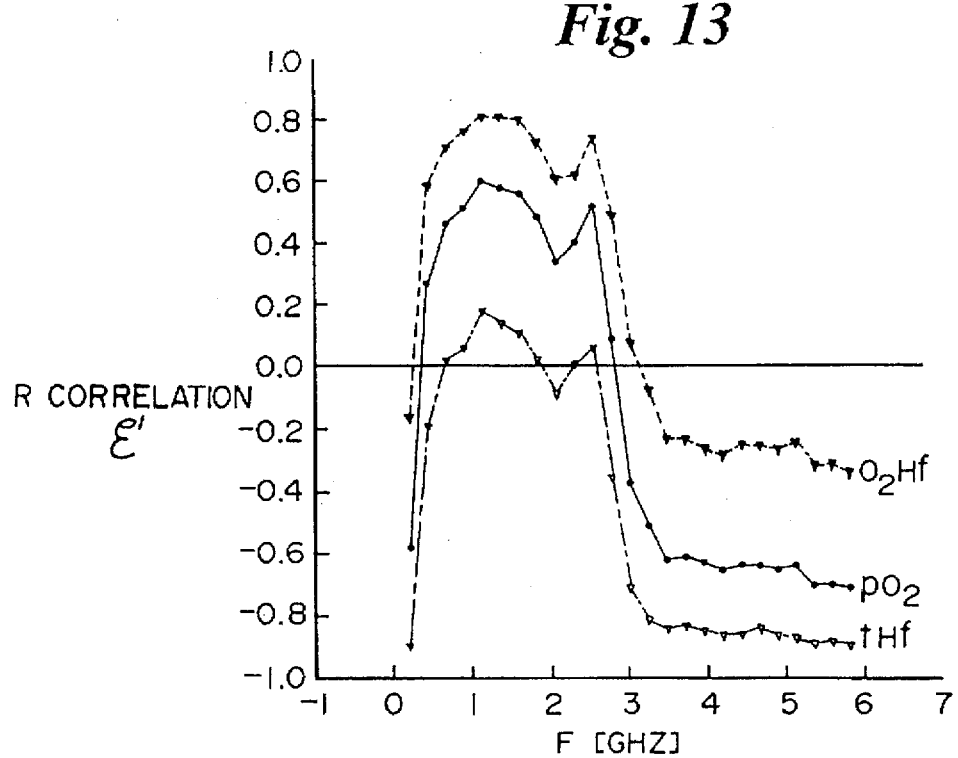
FIG. 13 is a graph of first order canine cardiac tissue dielectric characteristics correlated to frequency of microwave emission.
Figure 14:
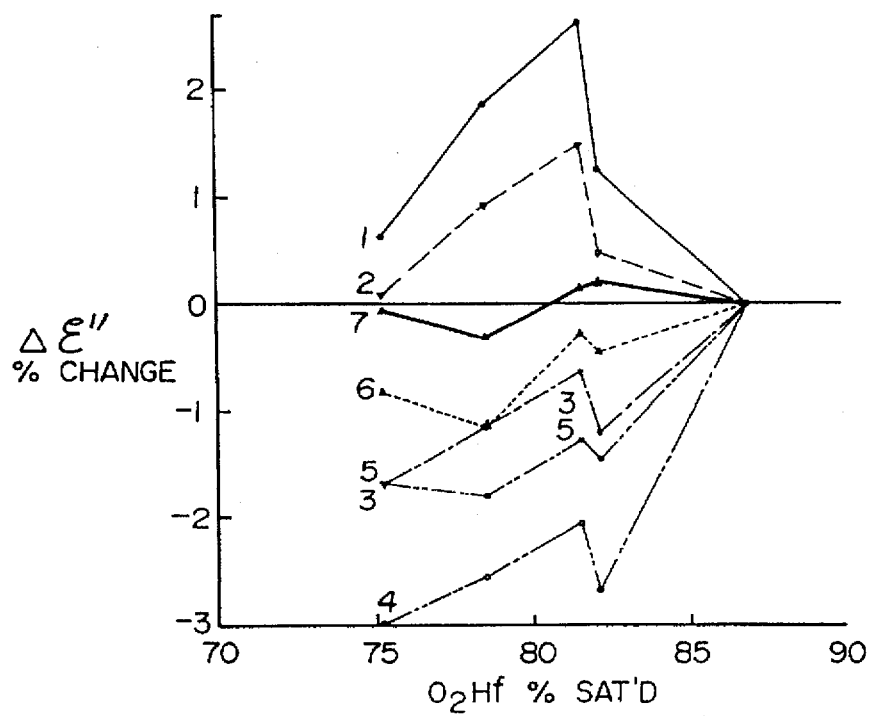
FIG. 14 is a graph of blood oxygen content correlated to second order canine cardiac tissue dielectric characteristics and frequency of microwave emissions.

FIGS. 13 and 14 disclose the correlation of dielectric characteristics to blood oxyhemoglobin content. In FIG. 13, the dielectric characteristic is the percent of $(\epsilon '(HbO_2)-\epsilon '(86.9))/\epsilon '(86.9)$, and in FIG. 14 the dielectric characteristic is the percent of $(\epsilon ''(HbO_2)-\epsilon ''(86.9))/\epsilon ''(86.9)$. In each figure the frequency curves 161, 163, 165, 167, 169, 171, and 173 correspond to 0.2 GHz, 1.14 GHz, 2.13 GHz, 3.12 GHz, 4.01 GHz, 5.0 GHz, and 6.0 GHz, respectively.

Figure 15:
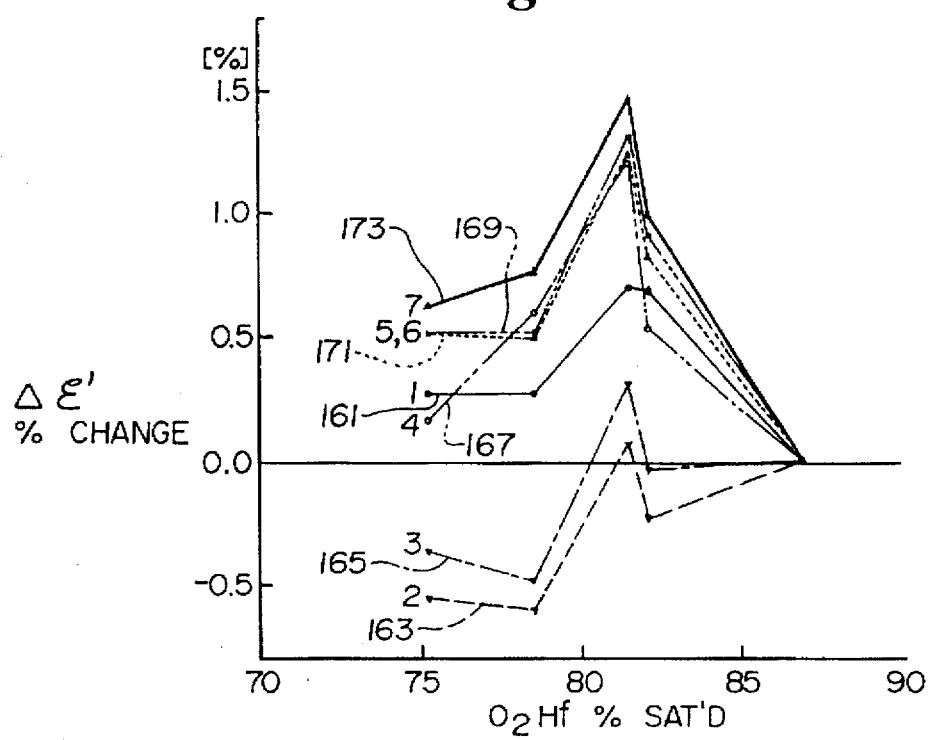
FIG. 15 is a graph of blood oxygen contents correlated to first order dielectric correlation coefficients and frequency of microwave emissions.

The dielectric permittivity of oxyhemoglobin ($HbO_2$), the partial pressure of oxygen ($PO_2$) and total hemoglobin (tHb) content are correlated to microwave frequency range 0.2–6 MHz in FIG. 15. The highest degree of correlation for oxyhemoglobin occurs between the frequency range 0.5–2.5 MHz. Through this range the dielectric permittivity value $\epsilon '$ is most sensitive to the oxyhemoglobin saturation content of blood.

Figure 16:
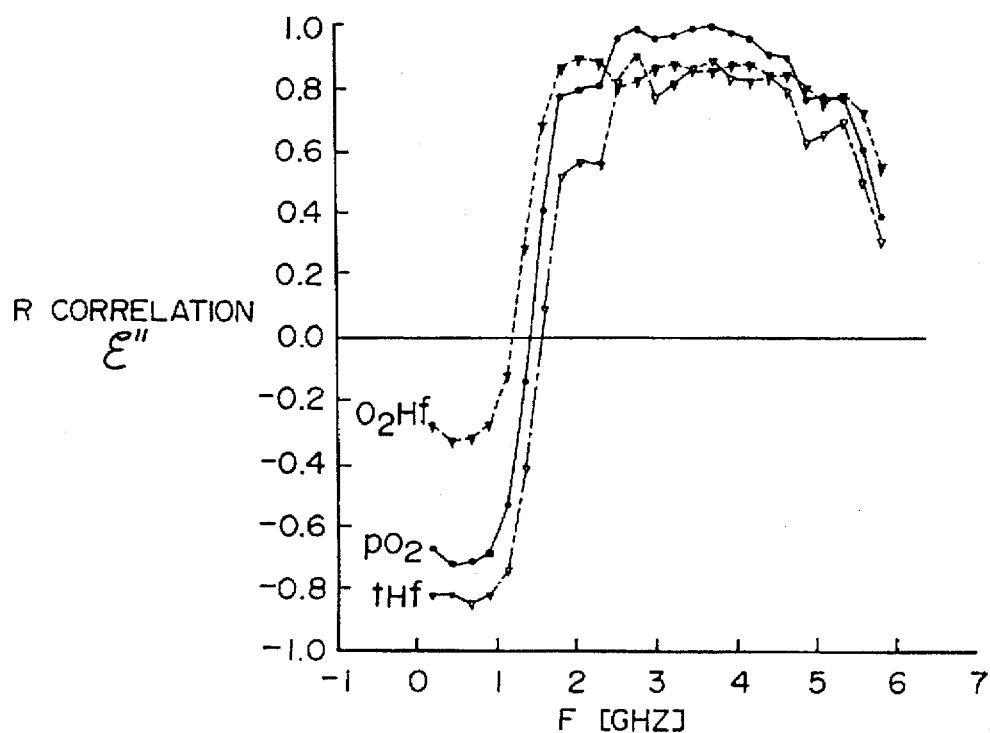
FIG. 16 is a graph of blood oxygen contents correlated to second order dielectric correlation coefficients and frequency of microwave emissions.

The correlation coefficient curve for $\epsilon ''$, dielectric loss, is disclosed in FIG. 16. The correlation coefficient for $HbO_2$ is highest at approximately 2 GHz with the correlation coefficient for $PO_2$ approaching unity between 2.5 and 4 GHz.

The correlation coefficient studies disclosed in FIGS. 15 and 16 are representative of the invention's ability to distinguish between oxyhemoglobin ($HbO_2$) saturation percentage and $PO_2$. Both of these values are important pieces of information useful to health care providers. Presently, there exists real time bed side photometric means for determining oxyhemoglobin saturation percentage called an oximeter. However, in order to obtain a $PO_2$ value, arterial blood must be withdrawn from a patient into specialized syringes and put through a machine capable of directly measuring the partial pressure of gases in a liquid.

Figure 17:
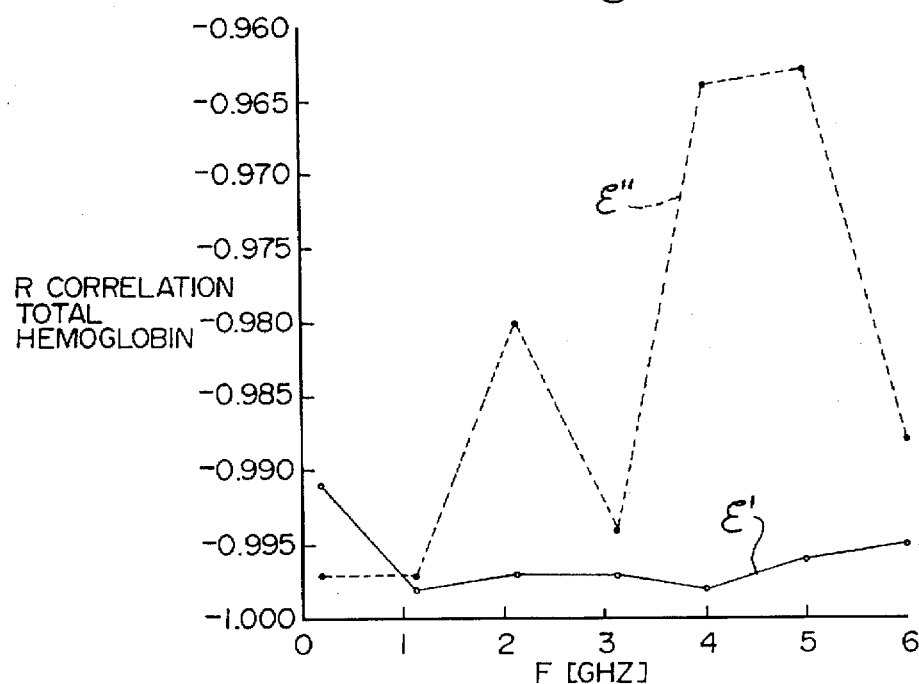
FIG. 17 is a graph of first order and second order dielectric coefficients correlated to total hemoglobin correlation coefficients and frequency of microwave emissions.

The $\epsilon '$ and $\epsilon ''$ curves for total hemoglobin as a reference correlation are depicted in FIG. 17. The $\epsilon '$ curve as shown is a fairly flat correlation curve that is fairly non-correlative, maintaining values of correlation less than −0.995 throughout most of the curve. The $\epsilon ''$ curve, however, shows an increase in correlation to total hemoglobin for the microwave frequency range between 4 and 5 GHz. As noted above in the discussions pertaining to FIGS. 3 and 4, correlation values for oxyhemoglobin $PO_2$ and total hemoglobin may accurately derive from these correlation curves during a single frequency range scan from 0.2–6 GHz and calculating the dielectric permittivity $\epsilon'$ and dielectric loss $\epsilon''$ values for blood. The concentration of oxyhemoglobin saturation would then be best correlated with the $\epsilon'$ value at, or about, 1.5 GHz, the $PO_2$ value would then be calculated from the correlation value of the dielectric loss, $\epsilon''$, calculated at, or about, 3.5 GHz, and tHb could be calculated from the correlation value of the dielectric loss curve, $\epsilon''$, calculated at, or about, 4.5 GHz. Each scan through the frequency range from 0.2–6 GHz would require no more than several milliseconds of microwave exposure and then computing the value calculations. Thus, the present invention could feasibly be used at the bedside for virtual real time assessment of these parameters.

The present invention is able to provide a real time bedside monitoring of $HbO_2$ saturation percentage and $PO_2$ values. The present invention does so without necessitating removal of blood from the patient and the delay and cost of sending the blood to the laboratory for analysis.

This invention is not limited to $HbO_2$ and $PO_2$ values. Any blood and tissue component possessing a dielectric contrast characteristic is capable of direct measurement and real time evaluation, non-invasively, using this invention. The present invention also possesses an ability to detect dielectric characteristic changes that occur in a tissue that is becoming diseased. By way of example, a weakened diseased aneurysmal portion of a ten year old male's left ventricle was repaired. During this repair the diseased portion was resected from the heart such that the diseased portion was removed entirely. This requires that the resection margins contain normal myocardium. The invention was used to evaluate this piece of resected heart tissue and the test results are presented in FIGS. 18–20.

Figure 18:
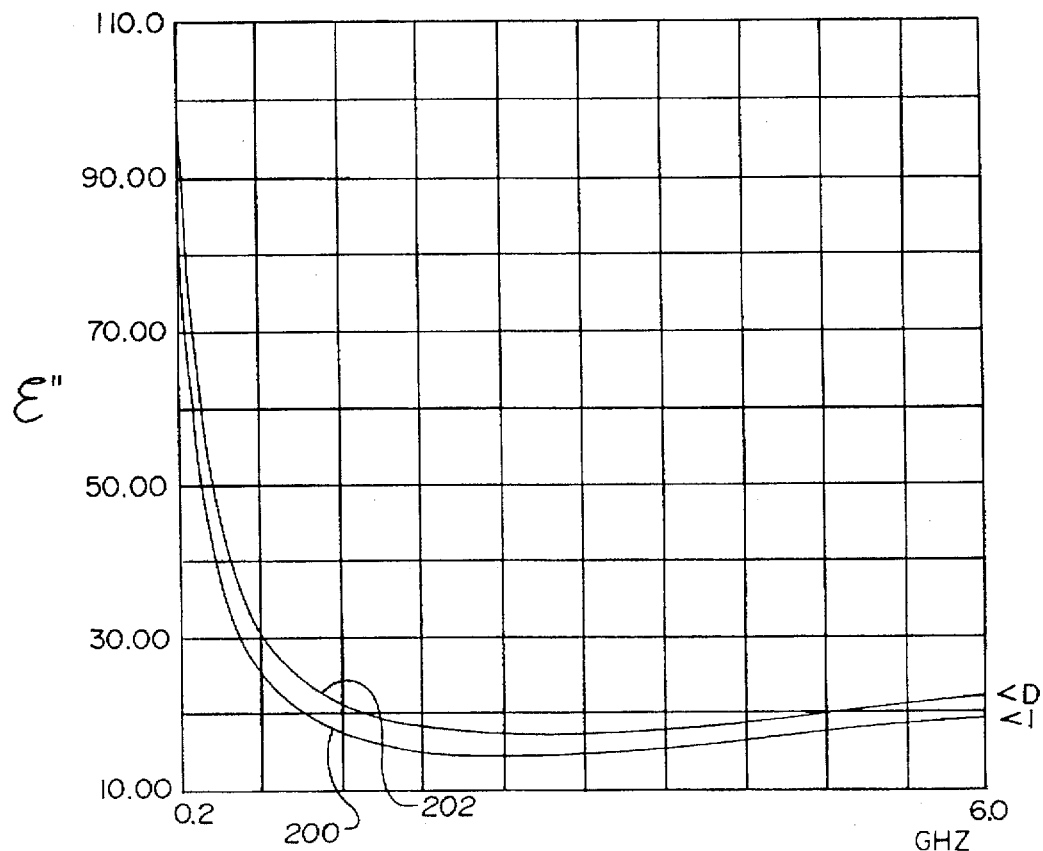
FIG. 18 is a graph of second order dielectric characteristics for a human left ventricular myocardium normal tissue to diseased tissue correlated by frequency of microwave emissions.

The $\epsilon''$ dielectric loss characteristic of normal myocardium is shown in FIG. 18 as a curve 200 measured over a microwave frequency range between 0.2 and 6 GHz. Throughout the entire frequency range this normal tissue is distinguishable from the abnormal tissue as shown by curve 202.

Figure 19:
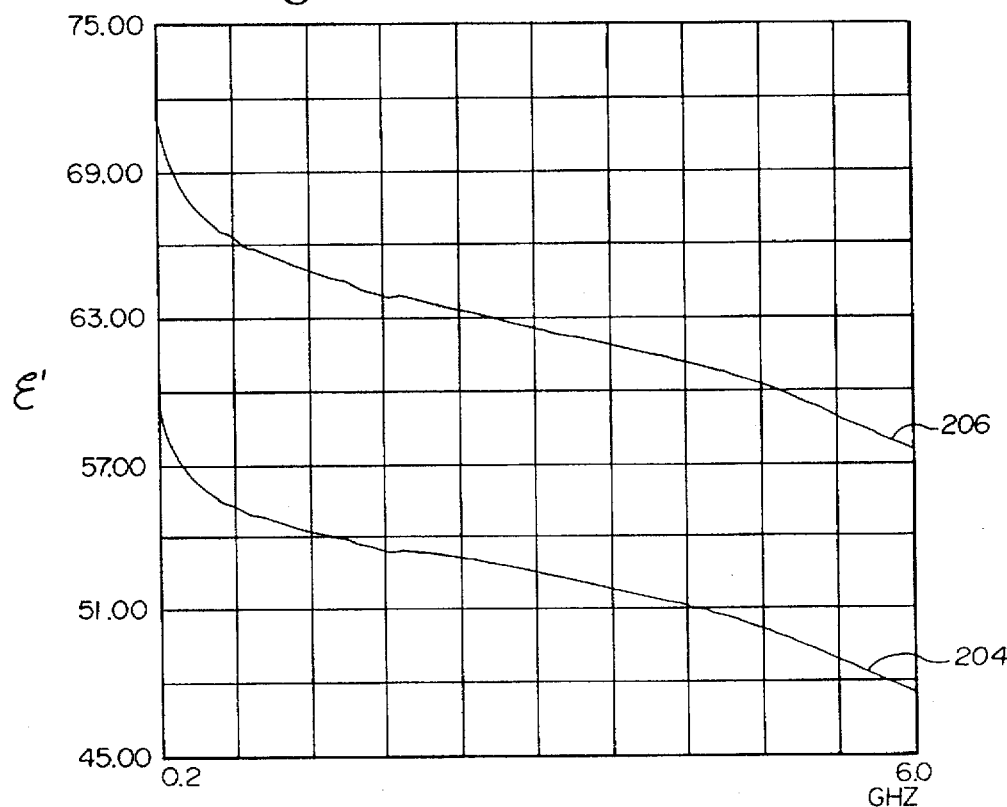
FIG. 19 is a graph of first order dielectric characteristics for a human left ventricular myocardium normal tissue to diseased tissue correlated by frequency of microwave emissions.

FIG. 19 shows the $\epsilon'$ dielectric permittivity characteristic curves for this same tissue sample. Normal tissue has a $\epsilon'$ single curve represented by curve 204. The abnormal tissue is shown in curve 206. The normal myocardial tissue is distinguishable from abnormal myocardial tissue over the entire microwave frequency range used in the present invention.

Figure 20:
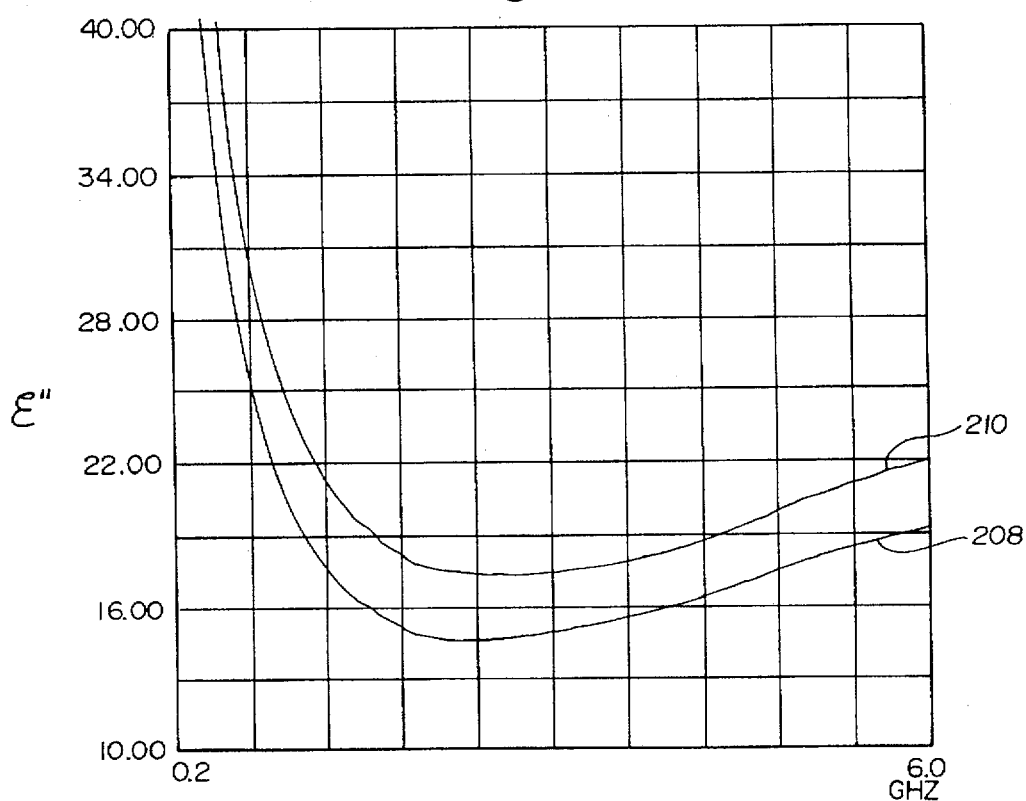
FIG. 20 is an expanded scale graph of the second order dielectric characteristics for a human left ventricular myocardium normal tissue to diseased tissue correlated by frequency of microwave emissions shown in FIG. 18.

FIG. 20 is an expanded scale graphic representation of the same $\epsilon''$ dielectric loss data of FIG. 18. Curve 208 represents the $\epsilon''$ for normal myocardial tissue with curve 210 representing the $\epsilon''$ values for abnormal cardiac tissue.

The present invention is able to use this dielectric characteristic difference to generate an image. For example, as system 10 of FIGS. 1–4 scans a patient's chest, an anatomical image of the organs is obtained based on the dielectric characteristic differences between the various tissues as demonstrated in FIGS. 5–12 and 18–20. Additionally, the invention facilitate anatomical location of diseased abnormal tissue within normal tissue. This anatomical information is useful in many ways. An example of one important use would be to direct real time therapy. Often abnormal myocardial tissue causes deleterious rhythm disturbances. Unfortunately, this abnormal tissue may be visually indistinguishable from surrounding normal myocardium. The present invention provides real time imaging of the abnormal tissue based on the dielectric characteristic differences such as those detected in FIGS. 18–20. Using fast reconstruction routines and scanning through the frequency range in at time rates that are fractions of the tissue event time cycle, a clinician creates a map of the abnormal tissue. Depending upon which frequency and dielectric characteristic is evaluated, the investigator may reconstruct the dielectric properties to generate a functional excitation map through the abnormal tissue area or alternatively may reconstruct a temporal change map and correlate those temporal changes to known electrical markers for anomalies within the tissue. The clinician may then direct ablation therapy to remove this abnormal rhythm focus and evaluate the adequacy of the tissue removal.

Figure 21:
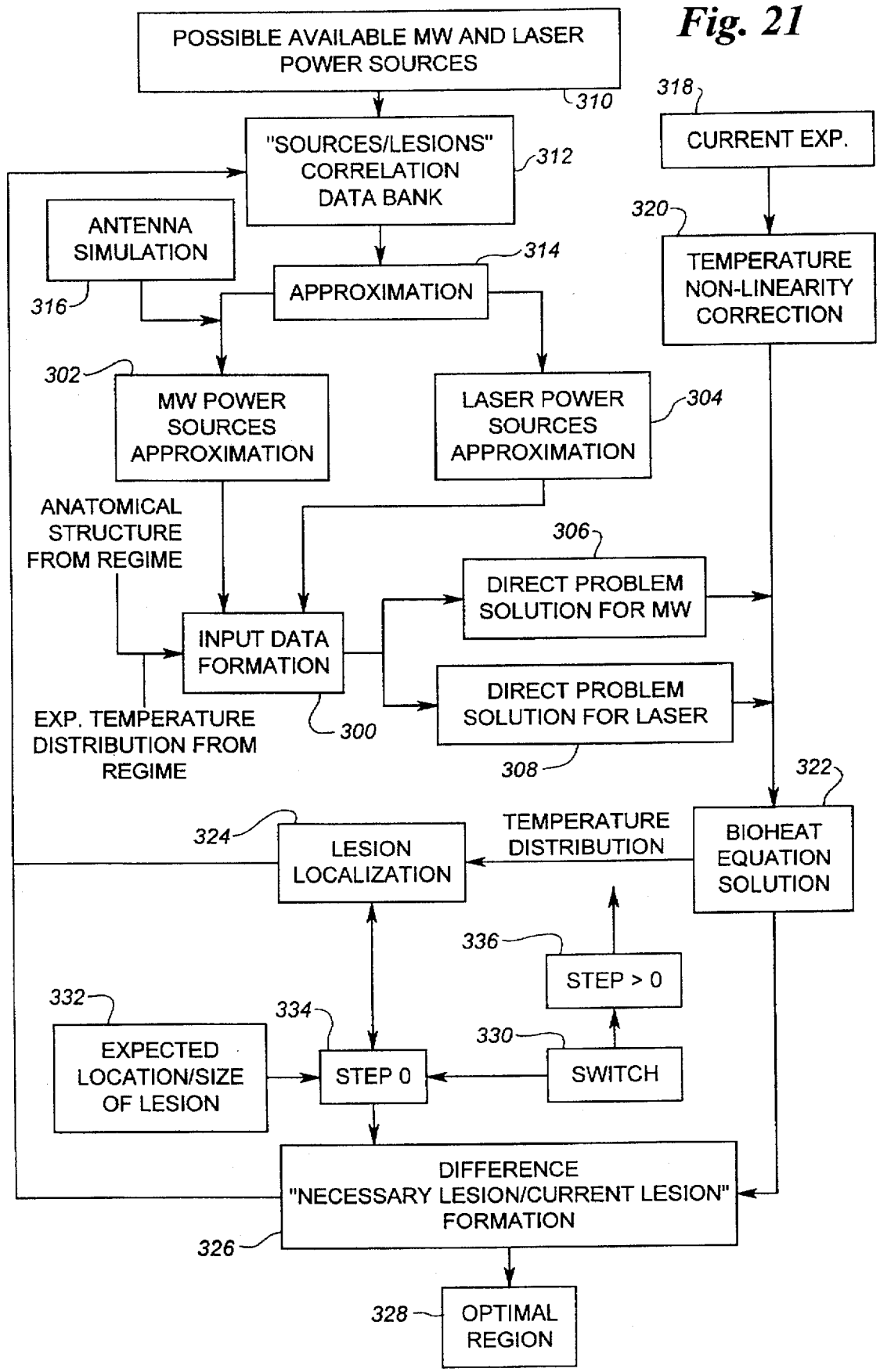
FIG. 21 is a flow diagram of an ablation choice algorithm.

An embodiment of the present invention using laser or microwave sources of ablation is disclosed in FIG. 21. As disclosed, a method for ablation of a lesion, for example, an arrhythmogenic focus within normal myocardial tissue, is performed beginning with inputing information into an input data formation step 300 from anatomical structure analysis derived from data generated by the invention disclosed in FIG. 2 and expected temperature distribution values. The input data formation step uses information from a microwave power source as an approximation step 302 or a laser power source as an approximation step 304 to derive input to be fed to a direct problem solution for microwave 306 or direct problem solution for laser control 308. A determination step for determining the possible available microwave and laser power sources is undertaken at step 310. The result of this determination is passed onto a sources and lesions correlation databank 312 to derive an approximation step 314, also taking input from an antenna simulation step 316. The current expected temperature is calculated at step 318 and corrected for a temperature non-linearity at step 320. The results of the direct problem solutions for microwave or laser 306, 308 in conjunction with the corrected current temperature from 320 is incorporated into a biological heat equation solution 322 to derive an actual temperature solution. Temperature distribution from the bioequation step 322 is passed to a lesion localization step 324 which provides data back to the source lesion correlation databank 312 for running the next approximation through to the input data formation 300 for the next determination of the bioheat equation solution step 322. Information from the equation solution step 322 is also passed to a different necessary lesion current lesion formation step for comparing the current lesion size with the estimated necessary lesion size to determine if optimum therapy has been achieved or not. If treatment has been achieved, the decision then passes to optimal region step 328. If the current lesion is different than the necessary lesion, the different information is passed back to step sources lesion correlation databank 312 for a reapproximation at step 314 on through input data formation 300 to undertake the next treatment in order to more closely approximate the necessary lesion through treatment. The number of steps through the iterative process are monitored by switch 330 with comparison of an expected location size of lesion step 332 at step 0, step 334. For steps greater than 0, switch 330 switches to step greater than zero step 336. The entire process is continuously re-evaluated for completeness of ablation therapy and re-evaluating on a real time basis the lesion generated by analysis of the anatomical structure derived from the microwave tomographic imaging system.

The invention provides for using microwave energy in a novel approach providing rapid real time assessment of biological function and anatomical structure by reverse problem solution for the dielectric characteristics of biological tissues. The invention achieves substantial increase in processing speed as well as substantial improvement in resolving power over any known prior art. The present invention also provides for techniques in evaluating real time parameters for determining biological component concentrations or physiologic characteristics based on the dielectric contrast between different states of physiologic activity for the biological compound or physiologic reaction.

We claim:

1. A system for non-invasive microwave tomographic spectroscopy of tissue, the system comprising:
   a) power source means for supplying microwave radiation;
   b) a plurality of microwave emitter-receivers spatially oriented to the tissue;
   c) an interface medium placed between the emitter-receivers;
   d) control means operably coupled between the power source means and the plurality of microwave emitter-receivers for selectively controlling power to the plurality of emitter-receivers and for receiving microwave signals from the plurality of emitter-receivers so that multiple frequency microwave radiation is emitted from a selected plurality of emitter-receivers and received by a selected plurality of emitter-receivers after interacting with and passing through the tissue;
   e) encoding means for encoding the microwave radiation supplied to the selected plurality of emitter-receivers so that when the microwave signals are received from the selected receiving plurality of emitter-receivers after interacting with the tissue, the signals are distinguishable by their originating emitter; and,
   f) computational means operably connected to the control means for computing a tomographic spectroscopic image of the tissue from the microwave signals received from the selected plurality of emitter-receivers.

2. The system of claim 1 in which the interface medium comprises a fluid having a preliminary dielectrically adjustable dielectric permittivity between about 50 and 90 at 2.45 GHz and a dielectric loss between about 5 and 25.

3. The system of claim 1 in which the multiple frequency microwave radiation is preferably within a range of about 0.2 GHz to about 5 GHz.

4. The system of claim 1 in which the multiple frequencies of microwave radiation are generated using pulse width emissions from one of the emitter-receivers, each emission having a power level so that the incident power density at the irradiating body is no more than about 1 mW/cm$^2$.

5. The system of claim 1 in which the plurality of microwave emitter-receivers comprises an array of emitter-receivers arranged in a circular configuration.

6. The system of claim 5 in which the emitter-receivers are radially adjustable relative to the circular array.

7. The system of claim 1 in which the plurality of microwave emitter-receivers comprises a plurality of stacked emitter-receivers arranged in a circular configuration.

8. The system of claim 1 in which the control means comprises means for selecting a multiple of emitter-receivers to act as emitters and a separate multiple of emitter-receivers to act as receivers.

9. The system of claim 1 in which the computational means comprises:
   a) an input data formation component for receiving and formatting data to be used in a direct problem solution component;
   b) a direct problem solution component configured to receive data from the input data formation component and to calculate an image of the biological tissue based on knowing what the amplitude and phase of the emitted microwave energy is and making an assumption as to what the biological tissue dielectric effects will be and calculating an expected amplitude and phase value for the transmitted microwave energy;
   c) a reverse problem solution component which receives the solution from the direct problem solution component and then calculates an image of the biological tissue based on known emitted microwave amplitude and phase values and known received amplitude and phase values from the emitter-receiver arrays; and
   d) a frequency correction component.

10. The system of claim 9 in which the reverse problem solution component comprises:
   a) a functional formation component configured to sum the inputs from all emitters-receivers;
   b) a gradient formation component configured for use as a derivative of the functional component to simplify processing speed;
   c) a minimization parameter tau calculation component configured to verify the accuracy of the gradient function and to allow image reconstruction in the most accurate manner; and
   d) an $\epsilon^*$ calculation component configured to calculate $\epsilon^*$ as a representative value of dielectric contrast between tissue regions or tissue physiologic states, where $\epsilon^* = \epsilon' + i\epsilon''$ and where $\epsilon'$ and $\epsilon''$ are the values of measured dielectric permittivity and dielectric loss and i represents the imaginary number.

11. The system of claim 1 in which the encoding means comprises means for altering the microwave radiation phase.

12. The system of claim 1 in which the encoding means comprises means for altering the microwave radiation amplitude.

13. The system of claim 1 in which the encoding means comprises means for altering the microwave radiation polarity.

14. A method for non-invasive microwave tomographic spectroscopy of tissue, the method comprising the steps of:
   a) providing a microwave radiation power source;
   b) providing a plurality of microwave radiation emitter-receivers;
   c) controlling the plurality of microwave radiation emitter-receivers so that a plurality of emitter-receivers are able to emit multiple frequency microwave radiation from the power source to a plurality of emitter-receivers that are receiving the microwave radiation;
   d) placing an interface medium between the emitting and receiving microwave emitter-receivers;
   e) placing tissue to be irradiated within the interface medium;
   f) encoding the microwave radiation which is to be emitted to distinguish an origin among the plurality of emitter-receivers and emitting the microwave radiation from the microwave emitter-receivers;
   g) receiving the microwave radiation in the microwave emitter-receivers after interacting with the tissue and decoding the received microwave radiation so that the origin of the received microwave radiation is distinguishable by the originating emitter; and
   h) measuring a change in the microwave radiation after interacting with the tissue.

15. The method of claim 14 in which the multiple frequency microwave radiation is simultaneously emitted from a plurality of emitter-receivers.

16. The method of claim 14 in which the measuring step includes the steps of solving the mathematical reverse problem to compute a tomographic image of the tissue based on the measured change of the microwave radiation, the reverse problem solution comprising the steps of:

a) determining a functional formation component;

b) calculating a derivative value of the functional formation component to create a gradient formation component useful for increasing the processing speed of the mathematical reconstruction calculations;

c) calculating a minimization parameter tau; and d) performing an $\in *$ calculation.

17. The method of claim 16 in which the $\in *$ calculation is a value derived by calculating the dielectric characteristics, $\in'$ and $\in''$, derived from the measured differences in the amplitude and phase changes of emitted and received microwave energy across a specified range, with the $\in *$ calculation functioning as a representative value of dielectric contrast between tissue regions or tissue physiologic states, where $\in * = \in' + i \in''$ and where $\in'$ and $\in''$ are the values of measured dielectric permittivity and dielectric loss and i represents the imaginary number.

18. A method of identifying discrete signals correlating to specific antenna arrays in a microwave tomographic spectroscopy tissue imaging system, comprising the steps of:

a) providing a microwave tomographic spectroscopy system having a microwave power source, a plurality of microwave emitters-receivers, an interface medium between the microwave emitters-receivers, control means for providing microwave signals to the emitters-receivers and for receiving microwave signals from the emitters-receivers after the microwave signals have interacted with the tissue;

b) orienting a tissue to be imaged in the interface medium;

c) encoding the signals originating simultaneously from different emitters and interacting with the tissue; and d) decoding the signals received by different receivers so that the signals are distinguishable according to the originating emitter.

19. The method of claim 18 in which the step of encoding comprises changing the phase of the microwave radiation.

20. The method of claim 18 in which the step of encoding comprises changing the amplitude of the microwave radiation.

21. The method of claim 18 in which the step of encoding comprises changing the polarization of the microwave radiation.

22. The method of claim 18 in which the step of encoding comprises changing the frequency of the microwave radiation.

23. A method of non-invasive microwave tomographic spectroscopy of tissue, the method comprising the steps of:

a) designating a target tissue area for microwave irradiation;

b) determining expected tissue dielectric values for the designated target tissue area;

c) providing a multiple frequency microwave radiation emitting and receiving system having microwave emission means comprising a plurality of emitter-receiver locations, microwave receiving means comprising a plurality of emitter-receiver locations, and microwave analysis means;

d) irradiating the target tissue area with the multiple frequency microwave radiation simultaneously emitted from a plurality of emitter-receiver locations;

e) receiving the microwave radiation from the irradiated target tissue area with the microwave receiving means; and f) analyzing the received microwave radiation with the microwave analysis means to obtain observed tissue dielectric values and comparing the observed tissue dielectric values with the expected tissue dielectric values to determine a physiologic state of the tissue within the designated target tissue area; the analyzing and comparing step including the step of solving the reverse problem to compute a tomographic image of the tissue based on the measured change of the microwave radiation, the reverse problem solution comprising the steps of determining a functional formation component, calculating a derivative value of the functional formation component to create a gradient formation component useful for increasing the processing speed of the mathematical reconstruction calculations, calculating a minimization parameter tau, and performing an E* calculation.

24. The method of claim 23 in which the comparing step comprises comparing the received microwave radiation in real time permitting real time determination of a changing physiologic state.

25. The method of claim 23 in which the determined physiologic state is a physiologic state selected from the list of physiologic states consisting of temperature, electrical excitation state, oxyhemoglobin saturation, blood oxygen content, total hemoglobin, blood gas partial pressures, ischemia, infarction, and myocardial viability.

26. The method of claim 25 in which the blood gas partial pressures include $PO_2$.

27. The method of claim 23 in which the designated target tissue area includes a patient's cardiac region to locate the origin of cardiac arrhythmias.

28. The method of claim 14, 18 or 23 further comprising the step of ablating designated tissue regions using an ablation catheter subsystem.

29. The method of claim 28 in which the ablation catheter subsystem uses laser energy for ablation.

30. The method of claim 28 in which the ablation catheter subsystem uses microwave energy for ablation.

31. The method of claim 28 in which the ablation catheter subsystem uses radio frequency energy for ablation.

32. The method of claim 27 in which the emitting and receiving steps are performed in time intervals which are a fraction of a tissue physiological event cycle time so that data acquisition relating to radiated tissue may occur many times during each tissue event.

33. A tomographic spectroscopic method of rapid non-invasive mapping of cardiac tissue to localize different physiologic states of the tissue, comprising the steps of:

a) designating a target cardiac tissue area for irradiation;

b) determining expected cardiac tissue dielectric values for the designated cardiac tissue area;

c) providing a multiple frequency radiation emitting and receiving system having radiation emission means comprising a plurality of emitter-receiver locations, radiation receiving means comprising a plurality of emitter-receiver locations, and radiation analysis means;

d) irradiating the target cardiac tissue area with the multiple frequency radiation simultaneously emitted from a plurality of emitter-receiver locations;

e) receiving the radiation from the irradiated target cardiac tissue area with the radiation receiving means;

f) analyzing the received radiation with the radiation analysis means to obtain observed tissue dielectric values and comparing the observed tissue dielectric values with the expected tissue dielectric values to determine the physiologic states of the tissue within the designated target tissue area; the analyzing and comparing step utilizing an $\epsilon*$ calculation which functions as a representative value of dielectric contrast between tissue regions or tissue physiologic states, where $\epsilon* = \epsilon' + i\epsilon''$ and where $\epsilon'$ and $\epsilon''$ are the values of measured dielectric permittivity and dielectric loss and i represents the imaginary number; and h) displaying a representation of the irradiated target cardiac tissue area on a display means so that different physiologic states of the tissue are recognizable.

34. The method of claim 33 in which the step of determining expected cardiac tissue dielectric values includes determination of values for ischemic tissue, scar tissue, and normal healthy tissue so that each tissue state is selectively displayable during the displaying step.

35. The method of claim 33 in which the analyzing and comparing step includes the step of solving the reverse problem to reconstruct tomographic biophysical images of the tissue based on the measured change of the radiation, the reverse problem solution step comprising the steps of:

a) determining a functional formation component;

b) calculating a derivative value of the functional formation component to create a gradient formation component useful for increasing the processing speed of the mathematical reconstruction calculations;

c) calculating a minimization parameter tau; and d) performing an E* calculation.

36. A method of detecting the onset of biological tissue disease comprising the method of:

a) designating a target tissue area for microwave irradiation;

b) determining expected tissue dielectric values for the designated target tissue area;

c) providing a multiple frequency microwave radiation emitting and receiving system having microwave emission means comprising a plurality of emitter-receiver locations, microwave receiving means comprising a plurality of emitter-receiver locations, and microwave analysis means;

d) irradiating the target tissue area with the multiple frequency microwave radiation simultaneously emitted from a plurality of emitter-receiver locations;

e) receiving the microwave radiation from the irradiated target tissue area with the microwave receiving means;

f) analyzing the received microwave radiation with the microwave analysis means to obtain observed tissue dielectric values and comparing the observed tissue dielectric values for a desired range of frequencies best correlating to the target tissue with the expected tissue dielectric values to determine a change in the physiologic state of the target tissue indicative of an onset of tissue disease; the analyzing and comparing step including the step of solving the reverse problem to reconstruct tomographic biophysical images of the tissue based on the measured change of the radiation, and the reverse problem solution step comprising the steps of determining a functional formation component, calculating a derivative value of the functional formation component to create a gradient formation component useful for increasing the processing speed of the mathematical reconstruction calculations, calculating a minimization parameter tau, and performing an E* calculation.

* * * * *